United States Patent [19]

Sato et al.

[11] Patent Number: 5,482,922
[45] Date of Patent: Jan. 9, 1996

[54] HERBICIDAL COMPOSITION EXHIBITING SYNERGISTIC ACTIVITY

[75] Inventors: Ryo Sato, Tokyo; Masako Kataoka, Minoo, both of Japan

[73] Assignee: Sumitomo Chemical Company Limited, Osaka, Japan

[21] Appl. No.: 47,052

[22] Filed: Apr. 12, 1993

Related U.S. Application Data

[62] Division of Ser. No. 867,077, Apr. 14, 1992, Pat. No. 5,238,901, which is a continuation of Ser. No. 336,085, Apr. 11, 1989, abandoned.

[30] Foreign Application Priority Data

Apr. 12, 1988 [JP] Japan .................................. 63-89563

[51] Int. Cl.$^6$ .......................... A01N 37/22; A01N 43/38; A01N 43/84
[52] U.S. Cl. .......................... 504/130; 504/149; 504/225; 504/341; 504/342; 71/DIG. 1
[58] Field of Search .................... 504/130, 149, 504/225, 342, 101, 341; 71/DIG. 1

[56] References Cited

U.S. PATENT DOCUMENTS

| 3,937,730 | 2/1976 | Vogel et al. | 564/214 |
| 4,640,707 | 2/1987 | Nagano et al. | 504/225 |
| 5,322,835 | 6/1994 | Takahashi et al. | 504/225 |

OTHER PUBLICATIONS

*The Agrochemicals Handbook,* Royal Society of Chemistry, (1983), p. A278/Oct. 1983.
"Noyaku Jikkenho (Methods in Pesticide Science)", 1981, pp. 109–112, published by Soft Science, Inc., Tokyo, including English translation thereof.

*Primary Examiner*—Richard L. Raymond
*Assistant Examiner*—John D. Pak

[57] ABSTRACT

A herbicidal composition which comprises as the active ingredients (a) 2-[7-floro-3,4-dihydro-3-oxo-4-(2-propynyl)-2H-1,4-benzooxazin-6-yl]-4,5,6,7-tetrahydro-1H-isoindol-1,3 (2H)-dione and (b) N-methoxymethyl-2',6'-diethyl-2-chloroacetanilide or 2-chloro-'6-ethyl-N-(2-methoxy-1-methylethyl)Acet-O-toluidide and an inert carrier or diluent, which exerts a synergistically enhanced herbicidal potency.

19 Claims, 2 Drawing Sheets

HERBICIDAL COMPOSITION EXHIBITING SYNERGISTIC ACTIVITY

This application is a divisional of application Ser. No. 07/867,077, filed on Apr. 14, 1992, now U.S. Pat. No. 5,238,901, which is a Rule 62 continuation application Ser. No. 07/336,085, filed on Apr. 11, 1989, now abandoned the entire contents of which are hereby incorporated by reference.

The present invention relates to a herbicidal composition. More particularly, it relates to a herbicidal composition comprising as the active ingredients (a) 2-[7-fluoro- 3,4-dihydro-3-oxo-4-(2-propynyl)-2H-1,4-benzooxazin- 6-yl]-4,5,6,7-tetrahydro-1H-isoindol-1,3(2H)-dione (hereinafter referred to as "Compound (I)") of the formula:

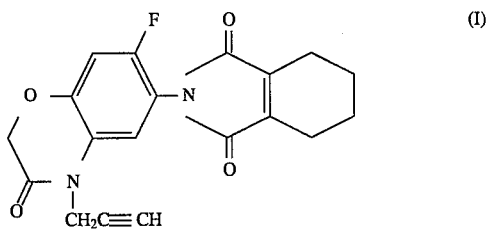

and (b) N-methoxymethyl-2',6'-diethyl-2-chloroacetanilide (hereinafter referred to as "alachlor") of the formula:

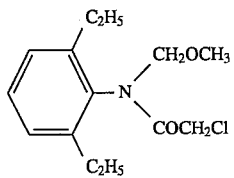

or 2-chloro-6'ethyl-N-(2-methoxy-1-methylethyl)acet-O-toluidide (hereinafter referred to as "metolachlor") of the formula:

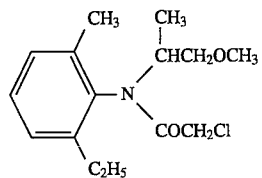

which exerts a highly enhanced herbicidal activity against a wide variety-of weeds without causing any material phytotoxicity to crop plants, particularly to peanut and soybean crops.

In recent years, a great number of chemicals having herbicidal activity have been used to exterminate or control undesired weed vegetation. Since, however, weeds are diversified in kind and their growth period extends over a long period of time, the herbicidal effects of conventional herbicidal agents are quite restricted in general. Consequently, the appearance of any herbicidal agent which exerts a strong herbicidal activity against a wide variety of weeds without any material phytotoxicity to crop plants has been highly desired.

As a result of extensive study, it has now been found that the associated use of Compound (I) and alachlor or metolachlor as the active ingredients produces a highly enhanced herbicidal activity against a wide variety of weeds without causing any material phytotoxicity to crop plants, particularly peanuts or soybeans. In comparison with the sole use of each of the active ingredients, enhancement of the herbicidal potency in their associated use is remarkable so that the active ingredients may be applied in smaller dosages. Thus, a clear and definite synergistic effect is observed in their associated use.

Figure 1:
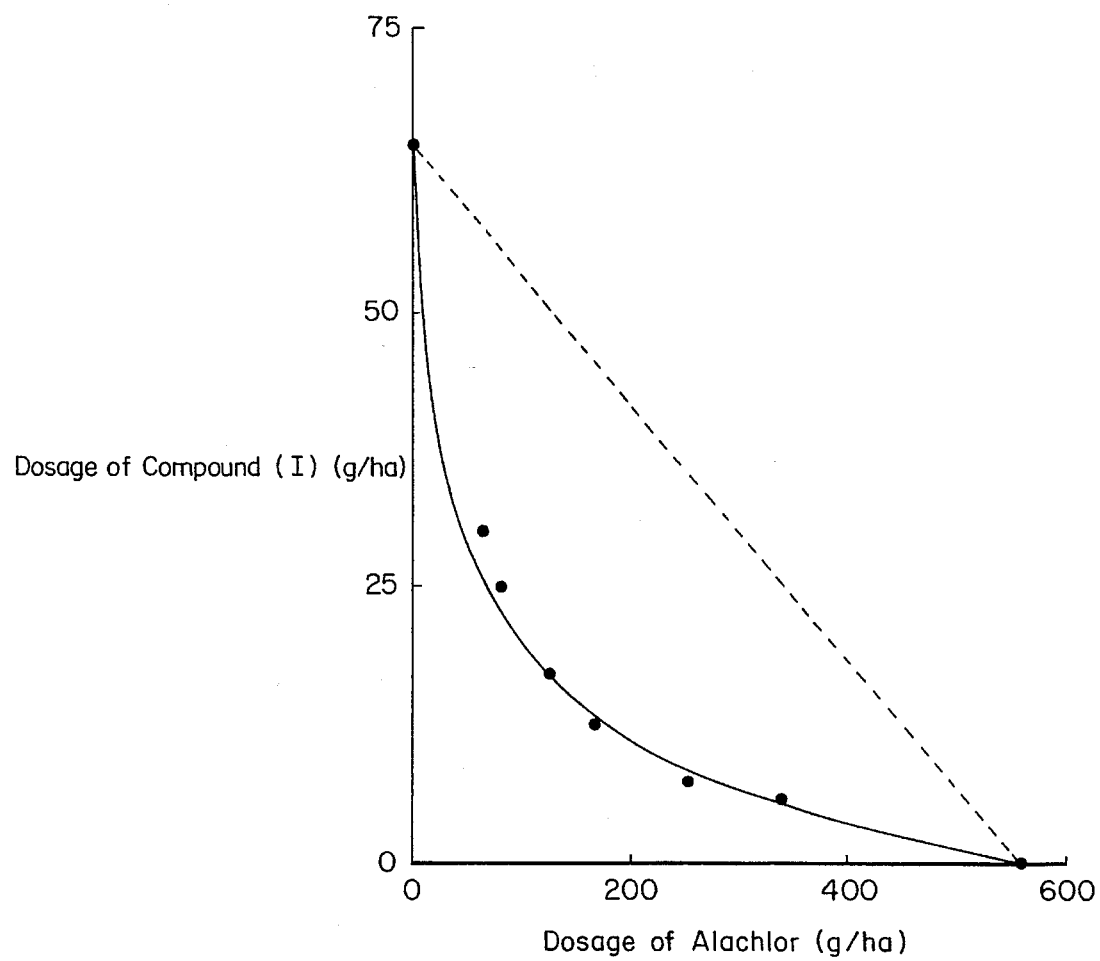
FIG. 1 is a graph of the dosages of compound (I) and alachlor which shows the equivalent efficacy line (i.e. solid line) and the arithmetic efficacy line (i.e. dotted line)

The herbicidal composition of the present invention which comprises Compound (I) and alachlor or metolachlor can exterminate or control a variety of weeds, e.g., dicotyledonus weeds such as wild buckwheat (*Polygonum convolvulus*), pale smartweed (Polygonum Laphathifolium), Pennsylvania smartweed (*Polygonum pensylvanicum*), common purslane (*Portulaca oleracea*), common lambsquarters (*Chenopodium album*), redroot pigweed (*Amaranthus retroflexus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), ivyleak morningglory (*Ipomoea hederacea*), tall morgingglory (*Pharbitis purpurea*), entireleaf morningglory (*Ipomoea hederacea v. integriuscula*), jimsonweed (*Datura stramonium*), black nightshade (*Solanum nigrum*), common cocklebur (*Xanthium strmarium*), common sunflower (*Helianthus annuus*), field bindweed (*Connvolvulus arvensis*), sun spurge (*Euphorbia nelioscopia*) and devils beggarticks (*Bidens frondosa*); monocotyledonus weeds such as barnyardgrass (*Echinochloa crus-galli*), green foxtail (*Setaria Viridis*), giant foxtail (*Setaria faberi*), yellow foxtail (*Setaria glauca*), souterhn crabgrass (*Digitaria ciliaris*), goosegrass (*Eleusine indica*), johnsongrass (*Sorghum halepense*), quackgrass (*Agropyron repens*), shattercane (*Sorghum bicolor*) and purple nutsedge (*Cyperus rotundus*), etc.

Compound (I) is known to exert a herbicidal activity (U.S. Pat. No. 4,640,707). Alachlor and metolachlor are also known to be useful as a herbicide (The Pesticide Mannual 7th Ed. p. 3 and p. 377, The British Crop Council, 1983). However, the associated use of Compound (I) and alachlor or metolachlor has never been attempted, and the production of a synergistic effect upon such conbined use has never been expected, The proportion of Compound (i) and alachlor or metolachlor as the active ingredients in the composition of the present invention may vary within a considerable broad range. Generally, however, alachlor or metolachlor may be used in an amount of about 2 to 100 parts by weight, preferably of about 4 to 60 parts by weight, to one part by weight of Compound (I).

In addition to the above active ingredients, the composition may contain a solid or liquid carrier or diluent. Any surface-active or auxiliary agent may also be incorporated therein. Thus, the composition may be formulated in any conventional preparation form such as an emulsifiable concentrate, wettable powder, suspension or granules. The combined content of the active ingredients in the composition may be from about 0.5 to 90% by weight, preferably from about 1 to 80% by weight.

As the solid carrier or diluent, there may be used kaolin clay, attapulgite clay, bentonite, terra alba, pyrophyllite, talc, diatomaceous earth, calcite, walnut-shell powder, urea, ammonium sulfate, synthetic hydrated silica, etc. Examples of the liquid carrier or diluent are aromatic hydrocarbons (e.g., xylene, methylnaphthalene), alcohols (e.g., isopropanol, ethylene glycol, cellosolve), ketones (e.g., acetone, cyclohexanone, isophorone), vegetable oils (e.g., soybean oil, cotton-seed oil), dimethylsulfoxide, acetonitrile, water, etc.

The surface-active agent used for emulsification, dispersion or spreading may be any of the anionic or non-ionic type of agents. Examples of the surface-active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments for preparation of the present composition are illustratively shown in the following Formulation Examples wherein part(s) are by weight.

FORMULATION EXAMPLE 1

Two parts of Compound (I), 50 parts of alachlor, 3 parts of calcium ligninsulfonate, 2 parts of sodium laurylsulfate and 43 parts of synthetic hydrated silica are well mixed while being powdered to obtain a wettable powder.

FORMULATION EXAMPLE 2

0.5 part of Compound (I), 20 parts of alachlor or metolachlor, 3 parts of polyoxyethylene sorbitan monooleate, 3 parts of CMC and 73.5 parts of water are mixed and pulverized until the particle size of the composition becomes less than 5 microns to obtain a suspension.

FORMULATION EXAMPLE 3

0.5 part of Compound (I), 10 parts of metolachlor, one part of synthetic hydrated silica, 2 parts of calcium ligninsulfonate, 30 parts of bentonite and 56.5 parts of kaolin clay are well mixed and pulverized. The resulting powder is admixed with water and dried to obtain granules.

A composition comprising Compound (I) and alachlor or metolachlor thus formulated is useful for pre-emergence control of undesired weeds by soil treatment. The soil treatment includes application to the soil surface prior to or after seeding or transplanting of the crop or incorporation into the soil before seeding. Direct application may be also adopted.

In order to improve the herbicidal activity, the composition may be used together with other herbicides. Besides, it may be used in combination with insecticides, acaricides, nematocides, fungicides, plant growth regulators, fertilizers, soil improvers, etc.

The dosage of the active ingredients may vary depending on prevailing weather conditions, soil involved, formulation used, mixing proportion of each active ingredient, crop and weed species, etc. In general, however, the total amount of Compound (I) and alachlor or metolachlor is favored to be within a range of about 50 to 4000 grams per hectare, preferably of about 200 to 2500 grams per hectare.

In case of the composition being formulated into an emulsifiable concentrate, a wettable powder or a suspension, it is normally diluted with water and applied over the top at a volume of about 10 to 1000 liters per hectare to the foliage of the crop plants or weeds which germinate or have germinated. The dilution may contain, in addition to the above mentioned surface active agent, any spreading or auxiliary agent such as polyoxyethylene resin acid esters, ligninsulfonates, abietic acid, dinaphthylmethane-disulfonates, paraffin and the like.

The practical herbicidal activity of the system of the invention will be explained in further detail with reference to the following Test Examples wherein the growth controlling percentage (%) was determined by weighing the aerial parts of the test plants (fresh weight) and making calculations according to the following equation:

$$\text{Growth controlling percentage (\%)} = \left\{ 1 - \frac{\text{Fresh weight of test plant in treated plot}}{\text{Fresh weight of test plant in untreated plot}} \right\} \times 100$$

The phytotoxicity to crop plants was visually observed.

Test Example 1

Seeds of soybean, peanut, green foxtail, southern crabgrass, barnyardgrass, redroot pigweed, black nightshade, velvetleaf and sicklepod were sown in a vat (area, 17×24 $cm^2$; height, 7 cm) filled with upland field soil. A designated amount of the composition in the form of a wettable powder formulated according to Formulation Example 1 was diluted with water and sprayed onto the soil at a spray volume of 1000 liters per hectare with the aid of a small hand sprayer. After 20 days' cultivation outdoors, the phytotoxicity and growth controlling percentage were observed. The results are shown in Table 1.

TABLE 1

| Active ingredient | Dosage (g/ha) | Mixing ratio (by weight) | Phytotoxicity Soybean | Peanut | Green foxtail | Southern crabgrass | Barnyardgrass | Redroot pigweed | Black nightshade | Velvetleaf | Sicklepod |
|---|---|---|---|---|---|---|---|---|---|---|---|
| Alachlor | 250 | — | None | None | 55 | 45 | 80 | 41 | 10 | 0 | 5 |
|  | 500 | — | None | None | 88 | 70 | 95 | 68 | 16 | 0 | 10 |
| Metolachlor | 250 | — | None | None | 65 | 60 | 85 | 93 | 18 | 0 | 12 |
|  | 500 | — | None | None | 88 | 78 | 97 | 100 | 25 | 0 | 16 |
| Compound (I) | 25 | — | None | None | 66 | 50 | 10 | 93 | 96 | 73 | 21 |
|  | 50 | — | None | Nonee | 85 | 63 | 58 | 100 | 100 | 95 | 40 |
| Compound (I) + Alachlor | 25 + 250 | 1:10 | None | None | 100 | 100 | 100 | 100 | 100 | 100 | 83 |
|  | 25 + 500 | 1:20 | None | None | 100 | 100 | 100 | 100 | 100 | 100 | 94 |
|  | 50 + 250 | 1:5 | None | None | 100 | 100 | 98 | 100 | 100 | 100 | 95 |
|  | 50 + 500 | 1:10 | None | None | 100 | 100 | 100 | 100 | 100 | 100 | 100 |

TABLE 1-continued

| Active ingredient | Dosage (g/ha) | Mixing ratio (by weight) | Phyto- toxicity Soy-bean | Peanut | Growth controlling percentage (%) Green fox-tail | Southern crab-grass | Barnyard-grass | Redroot pigweed | Black night-shade | Velvet-leaf | Sickle-pod |
|---|---|---|---|---|---|---|---|---|---|---|---|
| Compound (I) | 25 + 250 | 1:10 | None | None | 100 | 100 | 100 | 100 | 100 | 100 | 87 |
| + | 25 + 500 | 1:20 | None | None | 100 | 100 | 100 | 100 | 100 | 100 | 96 |
| Metolachlor | 50 + 250 | 1:5 | None | None | 100 | 100 | 100 | 100 | 100 | 100 | 98 |
|  | 50 + 500 | 1:10 | None | None | 100 | 100 | 100 | 100 | 100 | 100 | 100 |

Text Example 2

Seeds of green foxtail were sown in a vat (area, 10×16 cm²; height, 6 cm) filled with upland field soil. A designated amount of the composition in the form of a wettable powder formulated according to Formulation Example 1 was diluted with water and sprayed onto the soil at a spray volume of 1000 liters per hectare with the aid of a small hand sprayer. After 20 days' cultivation outdoors, the growth controlling percentage was observed. The results are shown in Tables 2 and 3.

TABLE 2

| | Growth controlling percentage of green foxtail (%) Compound (I) (g/ha) | | | | | |
|---|---|---|---|---|---|---|
| | 0 | 6.3 | 12.5 | 25 | 50 | 100 |
| Alachlor (g/ha) 0 | 0 | 21 | 45 | 66 | 85 | 97 |
| 63 | 12 | 43 | 55 | 85 | 98 | 100 |
| 125 | 35 | 64 | 84 | 96 | 100 | 100 |
| 250 | 58 | 83 | 98 | 100 | 100 | 100 |
| 500 | 88 | 97 | 100 | 100 | 100 | 100 |
| 1000 | 99 | 100 | 100 | 100 | 100 | 100 |

TABLE 3

| | Growth controlling percentage of green foxtail (%) Compound (I) (g/ha) | | | | | |
|---|---|---|---|---|---|---|
| | 0 | 6.3 | 12.5 | 25 | 50 | 100 |
| Meto- alachlor (g/ha) 0 | 0 | 21 | 45 | 66 | 85 | 97 |
| 63 | 13 | 45 | 75 | 88 | 97 | 100 |
| 125 | 45 | 70 | 86 | 95 | 100 | 100 |
| 250 | 63 | 85 | 96 | 100 | 100 | 100 |
| 500 | 88 | 95 | 100 | 100 | 100 | 100 |
| 1000 | 98 | 100 | 100 | 100 | 100 | 100 |

The results in Test Example 2 were analyzed according to the isobole (i.e., equivalent efficacy line) method [Vol. 3, Herbicides, pages 109–111 (1981) in "Noyaku Jikkenho" (Methods in Pesticide Science) edited by Junichi Fukami et al., Soft Science Inc., Tokyo] based on Tammes's method [Tammes, P. M. L.: Neth. J. Plant Path., 70, 73–80 (1964)]. Namely, several combinations of the compositions having different mixing ratios of Compound (I) and alachlor or metolachlor but exerting the same level of growth control effect, for example, 90% growth control, were plotted in a graph so as to readily determine a synergistic effect, an arithmetic effect or a competitive effect. In case of exhibiting a synergistic effect, the equivalent efficacy line as plotted is shown below the arithmetic efficacy line.

Figure 2:
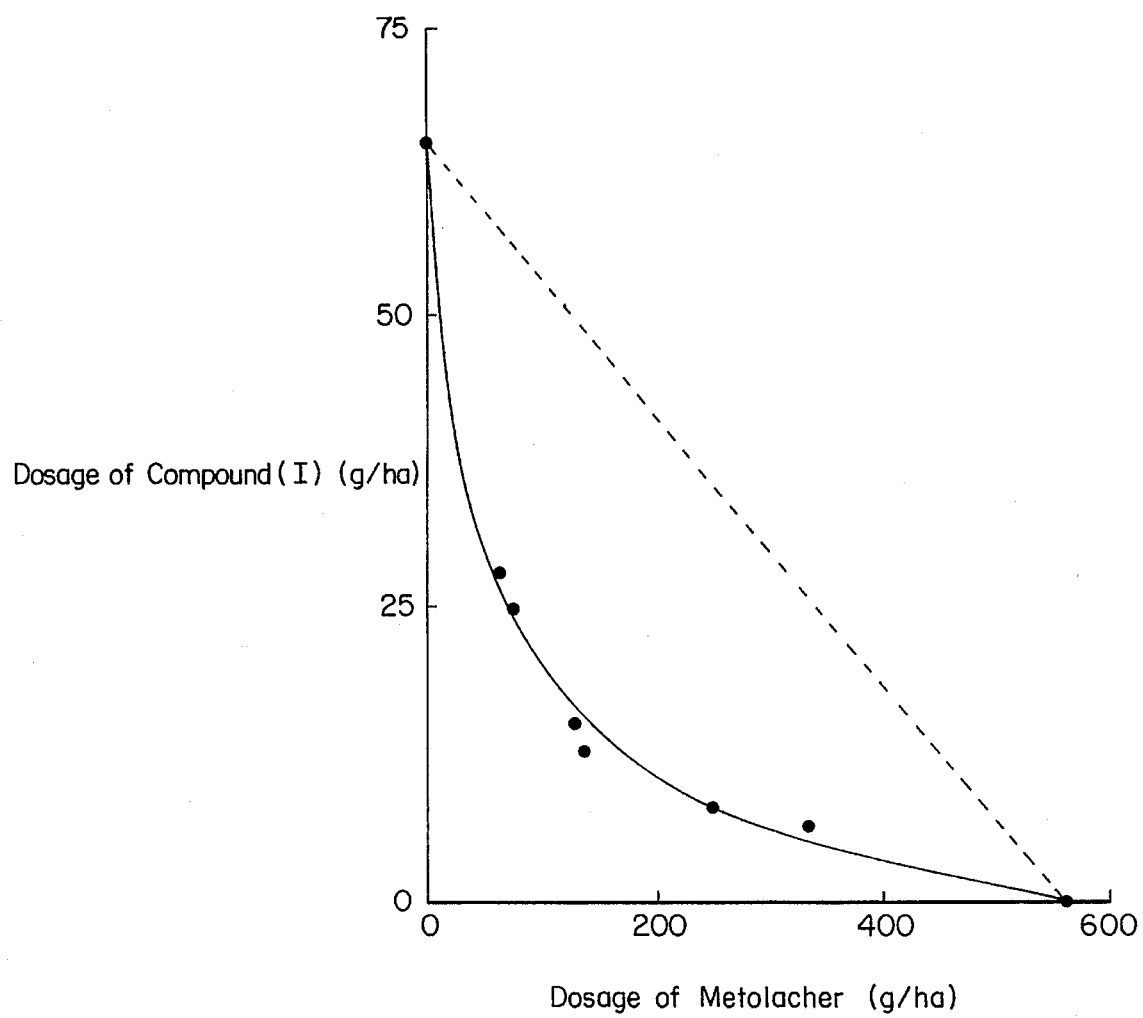
FIG. 2 is a graph of the dosages of compound (I) and metolachlor which shows the equivalent efficacy line (i.e. solid line) and the arithmetic efficacy line (i.e. dotted line).

Explaining further in detail with reference to the accompanying drawings, FIG. 1, wherein the ordinate indicates the dosage of Compound (I) and the abscissa indicates the dosage of alachlor, shows that the equivalent efficacy line (i.e., solid line) of 90% growth control of green foxtail is located below the arithmetic efficacy line (i.e., dotted line), from which it is understood that the associated use of Compound (I) and alachlor in a certain mixing ratio produces a synergistic effect; and FIG. 2, wherein the ordinate indicates the dosage of compound (I) and the abscissa indicates the dosage of metolachlor, shows that the equivalent efficacy line (i.e., solid line) of 90% growth control of green foxtail is located below the arithmetic efficacy line (i.e., dotted line), from which it is understood that the associated use of Compound (I) and metolachlor in a certain mixing ratio produces a synergistic effect.

What is claimed is:

1. A herbicidal composition which comprises a herbicidally effective amount of the combination of (a) 2-(7-fluoro-3,4-dihydro- 3-oxo-4-(2-propynyl)-2H-1,4-benzoxazin-6-yl)-4,5,6,7-tetrahydro-1H-isoindol- 1,3(2H)-dione of the formula:

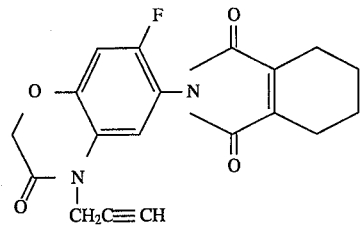

and (b) 2-chloro-6'-ethyl-N-(2-methoxy-1-methylethyl) acet-o-toluidide) of the formula:

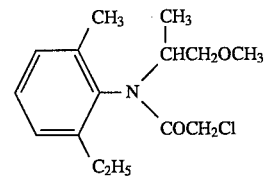

as the active ingredients, and an inert carrier or diluent, wherein the weight proportion of the components (a) and (b) is from 1:5 to 60.

2. The composition according to claim 1, wherein the weight proportion of the components (a) and (b) is from 1:5 to 40.

3. The composition according to claim 1, wherein the weight proportion of the components (a) and (b) is from 1: 10 to 40.

4. The composition according to claim 1, wherein the weight proportion of the components (a) and (b) is from 1:20 to 40.

5. A herbicidal composition which comprises a herbicidally effective amount of the combination of (a) 2-(7-fluoro-3,4-dihydro- 3-oxo-4-(2-propynyl)-2H-1,4-benzoxazin-6-yl)-4,5,6,7-tetrahydro-1H-isoindol- 1,3(2H)-dione of the formula:

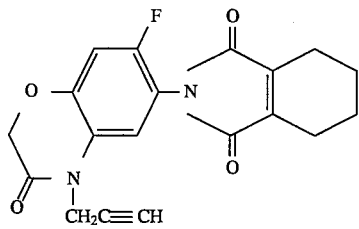

and (b) 2-chloro-6'-ethyl-N-(2-methoxy-1-methylethyl)acet-o-toluidide) of the formula:

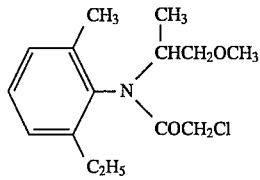

as the active ingredients, and an inert carrier or diluent, wherein the weight proportion of the components (a) and (b) is from 1:5 to 80.

6. The herbicidal composition according to claim 5, wherein the weight proportion of said components (a) and (b) is from 1:20 to 80.

7. The herbicidal composition according to claim 5, further comprising a surface-active or auxiliary agent.

8. The herbicidal composition according to claim 7, wherein said surface-active agent is selected from the group consisting of an anionic surface-active agent and a non-ionic surface active agent.

9. The herbicidal composition according to claim 7, wherein said surface-active agent is selected from the group consisting of an alkylsulfate, an alkylarylsulfonate, a dialkylsulfosuccinate, a phosphate of a polyoxyethylenealkylaryl ether, a polyoxyethylene alkyl ether, a polyoxyethylene alkylaryl ether, a polyoxyethylene polyoxypropylene block copolymer, a sorbitan fatty acid ester, and a polyoxyethylene sorbitan fatty acid ester.

10. The herbicidal composition according to claim 7, wherein said auxiliary agent is selected from the group consisting of a ligninsulfonate, sodium alginate, polyvinyl alcohol, gum arabic, carboxymethylcellulose, and isopropyl acid phosphate.

11. The herbicidal composition according to claim 5, wherein said herbicidal composition is in a form selected from the group consisting of an emulsifiable concentrate, a wettable powder, a suspension, and granules.

12. The herbicidal composition according to claim 5, wherein the combined content of said components (a) and (b) is from about 0.5% to 90% by weight.

13. The herbicidal composition according to claim 5, wherein the combined content of said components (a) and (b) is from about 1% to 80° by weight.

14. The herbicidal composition according to claim 5, wherein said inert carrier or diluent is selected from the group consisting of kaolin clay, attapulgite clay, bentonite, terra alba, pyrophyllite, talc, diatomaceous earth, calcite, walnut shell powder, urea, ammonium sulfate, synthetic hydrated silica, an aromatic hydrocarbon, an alcohol, a ketone, a vegetable oil, dimethylsulfoxide, acetonitrile, and water.

15. The herbicidal composition according to claim 14, wherein said aromatic hydrocarbon is selected from the group consisting of xylene and methylnaphthalene; said alcohol is selected from the group consisting of isopropanol, ethylene glycol, and cellosolve; said ketone is selected from the group consisting of acetone, cyclohexanone, and isophorone; and said vegetable oil is selected from the group consisting of soybean oil and cotton seed oil.

16. The method according to claim 15, wherein the total amount of said components (a) and (b) is from 50 to 4000 grams per hectare.

17. The method according to claim 15, wherein the total amount of said components (a) and (b) is from 200 to 2500 grams per hectare.

18. A method for controlling weeds, which comprises applying to weeds a herbicidally effective amount of a herbicidal composition which comprises a herbicidally effective amount of the combination of (a) 2-(7-fluoro-3,4-dihydro-3-oxo-4-( 2-propynyl)-2H-1,4-bezoxazin-6-yl)-4,5, 6,7-tetrahydro-1H-isoindol- 1,3(2H)-dione of the formula:

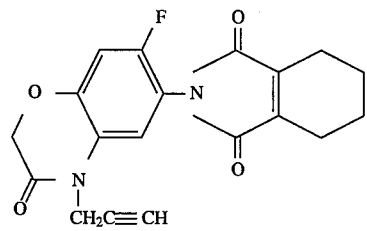

and (b) 2-chloro-6'-ethyl-N-(2-methoxy-1-methylethyl)acet-o-toluidide) of the formula:

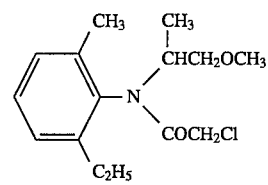

as the active ingredients, and an inert carrier of diluent, wherein the weight proportion of the components (a) and (b) is from 1:5 to 80.

19. The method according to claim 18, wherein said weeds are those germinated in a field of soybeans or peanuts.

* * * * *